United States Patent [19]

Mueller et al.

[11] Patent Number: 5,777,183

[45] Date of Patent: Jul. 7, 1998

[54] PROCESS FOR THE PRODUCTION OF GUERBET ALCOHOLS

[75] Inventors: Gerd Mueller, Duesseldorf; Bernhardt Gutsche, Hilden; Lutz Jeromin, Hilden; Udo Steinberner, Hilden; Reinhold Sedelies, Schifferstadt; Ralf Bohlander; Richard Ridinger, both of Duesseldorf; Dirk Springer, Haan; Franz Buettgen, Hilden; Frank Bartschik, Neuss, all of Germany

[73] Assignee: Henkel Kommanditgesellschaft auf Aktien, Duesseldorf, Germany

[21] Appl. No.: 676,029

[22] Filed: Jul. 5, 1996

[30] Foreign Application Priority Data

Jul. 4, 1995 [DE] Germany .................. 195 24 245.9

[51] Int. Cl.[6] .................................................. C07C 27/00
[52] U.S. Cl. ............................................................ 568/905
[58] Field of Search ......................... 568/905; 11/902

[56] References Cited

U.S. PATENT DOCUMENTS

| | | |
|---|---|---|
| 3,916,015 | 10/1975 | Yates ........................... 260/642 |
| 3,917,722 | 11/1975 | Yates ........................... 260/642 |
| 3,979,466 | 9/1976 | Yates . |
| 4,011,273 | 3/1977 | Aband . |

FOREIGN PATENT DOCUMENTS

| | | |
|---|---|---|
| 0 089 569 | 9/1983 | European Pat. Off. . |
| 855 107 | 11/1952 | Germany . |
| 14 43 666 | 9/1964 | Germany . |
| 2 363 000 | 12/1973 | Germany . |
| 26 34 676 | 2/1977 | Germany . |
| 27 03 746 | 8/1978 | Germany . |
| 40 14 736 | 11/1991 | Germany . |
| 1 433 986 | 4/1976 | United Kingdom . |

OTHER PUBLICATIONS

Angewandte Chemie 64 (1952) 213–220.

Primary Examiner—Gary Geist
Assistant Examiner—Karl J. Puttlitz, Jr.
Attorney, Agent, or Firm—Ernest G. Szoke; Wayne C. Jaeschke; Henry E. Millson, Jr.

[57] ABSTRACT

The invention relates to a process for the production of Guerbet alcohols by condensation of aliphatic alcohols in the presence of alkali metal or alkaline earth metal hydroxides as catalyst using the Guerbet reaction, in which the initial pressure in the reactor corresponds to the vapor pressure of the alcohol components used and, during the reaction, the pressure is continually reduced to the vapor pressure of the reaction mixture at the particular temperature.

20 Claims, No Drawings

PROCESS FOR THE PRODUCTION OF GUERBET ALCOHOLS

BACKGROUND OF THE INVENTION

1. Field of the Invention

This invention relates to a process for the production of Guerbet alcohols by condensation of aliphatic alcohols in the presence of alkali metal and/or alkaline earth metal hydroxide solutions as catalyst at a temperature of 180° to 280° C. and under a pressure which is adapted to the particular vapor pressure of the system. A co-catalyst is preferably added in liquid form by dissolution beforehand in alkali metal or alkaline earth metal hydroxide solution.

2. Statement of Related Art

The alkaline condensation of alcohols to relatively high molecular weight, branched isoalcohols was published for the first time by Guerbet in 1899. It involves a complete sequence of various reaction steps. In 1952, Machemer reported on the key steps of the reaction (Angewandte Chemie 64 (1952) 213–20). Besides dehydration to the ketone and aldol condensation, crotonization in which water is eliminated is an important step in the reaction sequence.

Various processes in which condensation of the alcohols is carried out in the presence of alkali metal or alkaline earth metal hydroxides and co-catalysts are known from the literature. For example, the joint use of potassium hydroxide, iron sulfate and basic copper carbonate is known from DE-C 27 03 746. Other combinations comprise the use of an alkaline catalyst with palladium compounds (GB-A 1,433,986), lead silicate, titanate and zirconate (DE-OS 26 34 676), copper chromite and Raney nickel (EP-A 0 089 569), zinc oxide (DE-PS 855 107, DE-OS 23 63 000) or organic zinc compounds (DE-OS 23 63 000). According to the teaching of DE-A1 40 14 736, the alkali metal or alkaline earth metal hydroxide may be used in solid form or in the form of an aqueous or alcoholic solution. The possibility of dissolving the co-catalyst beforehand in the alkali metal or alkaline earth metal hydroxide solution is also disclosed. In all the processes mentioned, however, the Guerbet reaction is initially very slow.

Methods for shortening the reaction time comprise removing water by stripping with nitrogen, using entraining agents, for example xylene or benzene, or water-binding agents (DE-OS 14 43 666). It is also known that the condensation rate increases with the increase in concentration of hydroxyl ions in the reaction mixture. However, since the percentage of unwanted oligomerization products clearly increases in the same way, this process is not a satisfactory solution to the problem.

In order to increase the reaction rate, the Guerbet reaction may even be carried out under a constant elevated pressure, cf. DE-PS 855 107 and DE-OS 2 363 000.

If the water of reaction is removed without entraining agents by continuous boiling (refluxing), a long initial phase is required to reach the reaction temperature in the guerbetization of relatively short-chain alcohols under normal pressure. In the guerbetization of 1-octanol, the required temperature of 245° C. is only reached at a percentage dimer content (2-hexyl decan-1-ol) of around 60%. The deviations between the boiling temperature and the required reaction temperature are even greater, for example, in the guerbetization of 1-hexanol. In view of the relatively long reaction time, however, a relatively high percentage of trimers is formed.

The complex problem addressed by the present invention was to provide a process for the production of Guerbet alcohols in which the reactor possession times are shortened, the yields are improved and, at the same time, the formation of trimers and soaps is minimized.

DESCRIPTION OF THE INVENTION

The present invention relates to a process for the production of Guerbet alcohols by condensation of aliphatic alcohols in the presence of alkali metal and/or alkaline earth metal hydroxides as catalysts using the Guerbet reaction, in which the initial pressure in the reactor corresponds to the vapor pressure of the alcohol components used and, during the reaction, the pressure is continually reduced to the vapor pressure of the reaction mixture at the particular temperature.

It has surprisingly been found that, providing the Guerbet reaction is carried out with suitable pressure control, the reaction rate can be significantly increased in relation to the prior art, so that better yields can be obtained for shorter reactor possession times. At the same time, fewer secondary products, for example Guerbet trimers and soaps, are obtained. In addition, by using co-catalyst dissolved beforehand in aqueous alkali metal or alkaline earth metal hydroxide solution, the reactor possession times can be further shortened and, at the same time, the quality of the products improved.

Process

In the practical application of the process, the reactor pressure is adapted to the particular vapor pressure of the reaction mixture. The vapor pressure P of the mixture can be calculated as follows in accordance with the equation known from thermodynamics:

$$P = X_M Y_M P_M^s + X_D Y_D P_D^s + X_W Y_W P_W^s \tag{1}$$

where x is the mole fraction, $P^s$ is the vapor pressure of the pure substance and
y is the activity coefficient. The index M denotes the monomer alcohol and the index D the dimer alcohol.

If, in very approximate terms, the water content (index W) is disregarded and if an ideal mixture with y=1 is considered, the following equation for determining the vapor pressure as a function of the conversion U is obtained for the educt/product system as a binary system:

From $$U = X_M^\circ - X_M = X_D \tag{2}$$

with $$X_M^\circ = 1 \tag{3}$$

and $$X_M + X_D = 1 \tag{4},$$

the required reactor pressure P is:

$$P = P_M^s \cdot X_M + (P_D^s - P_M^s) \cdot U \tag{5}.$$

Taking into account the approximations mentioned above, there is thus a linear correlation between the conversion and the reactor pressure. The conversion can be determined from the water of reaction accumulating and the particular reactor pressure to be established can be calculated from the conversion in accordance with equation (5). The reactor pressure is established in stages. In one preferred embodiment, the reactor pressure is automatically established through a control system. The quantity of water of reaction accumulating and distilled off is determined by a measuring system which transmits a signal to the automatic control system.

The process may be carried out at a temperature of 180° to 280° C. and is preferably carried out at a temperature of 240° to 260° C. It is largely independent of the alkali metal hydroxide solution/alkaline earth metal hydroxide solution/co-catalyst system and may be applied to various alcohols.

Catalysts

The process according to the invention for the production of Guerbet alcohols is generally carried out in the presence of 1 to 20% by weight and preferably 1.5 to 10% by weight, based on the alcohol, of alkali metal or alkaline earth metal hydroxide as catalyst. Alkali metal and alkaline earth metal hydroxides may be used in solid form, as flakes or pellets and as 25 to 80% by weight aqueous or alcoholic alkali metal or alkaline earth metal hydroxide solutions. It is of advantage to use concentrated solutions to avoid any unnecessary input of water. 40 to 60% by weight aqueous solutions are preferably used. A particularly preferred embodiment is characterized by the use of a 50% by weight aqueous potassium or sodium hydroxide solution.

Co-catalysts

Typical co-catalysts, which may be used individually or in combination in accordance with the invention, are chromium(III) salts, manganese(II) salts, iron(II) salts, cobalt(II) salts, lead(II) salts, tin oxide. In one particularly preferred embodiment, zinc oxide is used as the co-catalyst. The salts in question are water-soluble or alcohol soluble salts, preferably sulfates. The co-catalyst is preferably used in a concentration of 0.05 to 1% by weight, based on the alcohol to be reacted. In one particularly advantageous embodiment, the co-catalyst is used in a concentration of 0.1 to 0.5% by weight.

It is also of advantage to use the co-catalyst dissolved beforehand in the aqueous alkali metal or alkaline earth metal hydroxide solution. One particularly preferred embodiment is characterized by the use of an aqueous solution containing 3 to 10% by weight of co-catalyst and 40 to 60% by weight of alkali metal or alkaline earth metal hydroxide. Even where the Guerbet reaction is carried out with no pressure control, the use of predissolved co-catalysts leads to an improved yield in relation to the prior art for shorter reactor possession times and a higher quality of the products obtained.

Alcohols

Alcohols suitable for the production of the Guerbet alcohols are branched or unbranched, primary aliphatic alcohols containing more than 4 carbon atoms, preferably 6 to 22 carbon atoms, and/or cyclic alcohols containing more than 5 carbon atoms and technical mixtures thereof. Typical examples are hexanol, octanol, decanol, isotridecyl alcohol, dodecanol, myristyl alcohol, cetyl alcohol, palmitoleyl alcohol, stearyl alcohol, isostearyl alcohol, oleyl alcohol, elaidyl alcohol, petroselinyl alcohol, linolyl alcohol, linolenyl alcohol, gadoleyl alcohol, arachidyl alcohol, behenyl alcohol, erucyl alcohol, cyclohexanol, 2-ethyl hexan-1-ol. Saturated alcohols containing 6 to 10 carbon atoms are particularly preferred.

Commercial Applications

Introduction of the alkyl branch provides the Guerbet alcohols with characteristic physicochemical properties, such as a lower vapor pressure than the linear alcohols of comparable consistency. Melting point and viscosity are distinctly reduced in relation to linear alcohols. In addition, Guerbet alcohols have the advantage over the similarly liquid unsaturated alcohols that they are stable to oxidation and rancidity. Accordingly, the relatively short-chain Guerbet alcohols are particularly suitable for use as an oil component in pharmaceutical and cosmetic formulations, as plasticizers for synthetic resins, as lubricant components and as solvents or solubilizers for printing inks. The relatively high molecular weight Guerbet alcohols are particularly suitable for use as esterification components for special waxes and for the production of cosmetic stick preparations.

The following Examples are intended to illustrate the invention without limiting it in any way.

EXAMPLES

The tests were carried out in a stirred tank reactor surmounted by a condenser. The water of reaction was removed from the circuit by a phase separator and the alcohol phase was recycled. The system pressure was established through a control valve and blanketing with nitrogen. The reactor was heated by a heat exchanger.

Example 1

170 kg (1.3 kmoles) of 1-octanol, 0.143 kg (1.76 moles) of zinc oxide and 4.25 kg (75.76 moles) of potassium hydroxide (solid) were introduced into the reactor and reacted at normal pressure. The parameters temperature and pressure and the results are set out in Table 1.

Example 2

The same substances as in Example 1 were reacted with one another in the same molar ratios under a constant elevated pressure of 3 bar. The results and the test parameters are again set out in Table 1.

Example 3

The same substances as in Example 1 were again reacted in the same molar ratios. The reaction was carried out under an initial pressure of 3.5 bar which was reduced during the reaction to a final pressure of 750 mbar in accordance with the accumulation of distillate. The results are set out in Table 1.

Example 4

The same educts were used in the same molar quantities as in Example 1. However, a 50% by weight aqueous potassium hydroxide solution was initially prepared, the zinc oxide being dissolved therein. This liquid catalyst mixture was then added to the alcohol. The guerbetization was carried out under an initial pressure of 3.5 bar which was reduced to a final pressure of 650 mbar during the reaction in accordance with the accumulation of distillate. The results of the reaction are set out in Table 1.

Example 5

The reactants mentioned in Example 1 were reacted in the same molar ratios in a 350 liter reactor. Starting out from a reactor pressure of 6 bar, the pressure was reduced in stages (determined from the accumulation of distillate) to 1000 mbar. A conversion of 92% was reached after 15 hours. The yield of dimer amounted to 73.2% and the yield of trimer to 15.3%.

Example 6

95.5 kg (0.735 kmoles) of 2-ethyl hexan-1-ol and 23.3 kg (0.233 kmoles) of cyclohexanol were initially introduced into the reactor with 0.160 kg (1.97 moles) of ZnO and 2.0 kg (35.65 moles) of KOH. Starting out from a reactor pressure of 4.5 bar, the pressure in the reactor was reduced in stages to 1.8 bar. A conversion of 100% based on cyclohexanol was reached after 15 hours.

TABLE 1

Parameters and Results for Guerbetization in Accordance with Examples 1 to 4

| Example | Conditions | Time [h] | | | | | | |
|---|---|---|---|---|---|---|---|---|
| | | 3 | 5 | 8 | 10 | 15 | 20 | 30 |
| 1 | T [°C.] | 200 | 200 | 205 | 210 | 235 | 245 | 245 |
| | p [bar] | 1 | 1 | 1 | 1 | 1 | 1 | 1 |
| | Dimer [% by weight] | 4 | 8 | 13 | 17 | 38 | 57 | 66 |
| | Trimer [% by weight] | 0.6 | 1.0 | 2.6 | 3.0 | 4.8 | 9.2 | 10 |
| 2 | T [°C.] | 245 | 245 | 245 | 245 | 245 | 245 | |
| | p [bar] | 3 | 3 | 3 | 3 | 3 | 3 | |
| | Dimer [% by weight] | 43 | 50 | 53 | 55 | 57 | 58 | |
| | Trimer [% by weight] | 1.0 | 1.3 | 2.7 | 3.1 | 4.5 | 9 | |
| 3 | T [°C.] | 245 | 245 | 245 | 245 | 245 | | |
| | p [bar] | 3 | 1.5 | 1.0 | 0.75 | 0.75 | | |
| | Dimer [% by weight] | 43 | 57 | 63 | 68 | 70 | | |
| | Trimer [% by weight] | 0.9 | 1.5 | 2.3 | 2.6 | 4.0 | | |
| 4 | T [°C.] | 245 | 245 | 245 | 245 | 245 | | |
| | p [bar] | 2 | 1 | 0.75 | 0.65 | 0.65 | | |
| | Dimer [% by weight] | 54 | 69 | 78.8 | 80.3 | 83 | | |

What is claimed is:

1. A process for the production of Guerbet alcohols comprising the steps of

A) initiating the condensation of at least one aliphatic alcohol in the presence of at least one alkali metal hydroxide and/or alkaline earth metal hydroxide as catalyst, wherein the initial reaction pressure corresponds to about the vapor pressure of the at least one aliphatic alcohol; and B) continuing the condensation of the at least one aliphatic alcohol while continually reducing the reaction pressure to about the vapor pressure of the reaction mixture during the course of the reaction.

2. The process of claim 1 wherein the at least one aliphatic alcohol is at least one branched or unbranched primary aliphatic alcohol containing from 6 to 22 carbon atoms and/or cyclic alcohol containing at least 6 carbon atoms.

3. The process of claim 1 wherein the catalyst is present in from about 1 to about 20% by weight, based on the weight of the at least one aliphatic alcohol.

4. The process of claim 1 wherein the catalyst is an aqueous alkali metal hydroxide or alkaline earth metal hydroxide solution.

5. The process of claim 1 wherein a co-catalyst is also present which had been predissolved in an aqueous alkali or alkaline earth metal solution.

6. The process of claim 5 wherein the co-catalyst is at least one water-soluble or alcohol-soluble salt selected from the group consisting of chromium(II) salts, manganese(II) salts, Fe(II) salts, cobalt(II) salts, lead(II) salts, tin oxide, and zinc oxide.

7. The process of claim 5 wherein from about 0.05 to about 1% by weight of co-catalyst is present, based on the weight of the at least one aliphatic alcohol.

8. The process of claim 6 wherein from about 0.05 to about 1% by weight of co-catalyst is present, based on the weight of the at least one aliphatic alcohol.

9. The process of claim 6 wherein the catalyst is an aqueous solution containing from about 40 to about 60% by weight of the catalyst and from about 3 to about 10% by weight of the co-catalyst.

10. The process of claim 1 wherein the condensation reaction is carried out at a temperature of from about 180° to about 280° C.

11. The process of claim 10 wherein the temperature is from about 240° to about 260° C.

12. The process of claim 1 wherein the reaction pressure is automatically established by use of an automatic control system.

13. The process of claim 1 wherein water of reaction is distilled off during the condensation reaction.

14. The process of claim 12 wherein water of reaction is distilled off during the condensation reaction and determined by a measuring system which transmits a signal to the automatic control system.

15. The process of claim 3 wherein the catalyst is present in from about 1.5 to about 10% by weight.

16. The process of claim 1 wherein the at least one aliphatic alcohol is at least one saturated aliphatic alcohol containing from 6 to 10 carbon atoms.

17. The process of claim 8 wherein the co-catalyst is present in from about 0.1 to about 0.5%.

18. The process of claim 1 wherein the at least one aliphatic alcohol is at least one branched or unbranched primary aliphatic alcohol containing from 6 to 22 carbon atoms and/or cyclic alcohol containing at least 6 carbon atoms; the catalyst is present in from about 1 to about 20% by weight, based on the weight of the at least one aliphatic alcohol; and the condensation reaction is carried out at a temperature of from about 180° to about 280° C.

19. The process of claim 18 wherein from about 0.05 to about 1% by weight of a co-catalyst is present, based on the weight of the at least one aliphatic alcohol, and wherein the co-catalyst is at least one water-soluble or alcohol-soluble salt selected from the group consisting of chromium(II) salts, manganese(II) salts, Fe(II) salts, cobalt(II) salts, lead (II) salts, tin oxide, and zinc oxide.

20. The process of claim 18 wherein the pressure is automatically established by use of an automatic control system, and wherein water of reaction is distilled off and determined by a measuring system which transmits a signal to the automatic control system.

* * * * *